United States Patent
Mohr

(10) Patent No.: US 6,924,405 B2
(45) Date of Patent: Aug. 2, 2005

(54) XYLENE ISOMERIZATION

(75) Inventor: Gary David Mohr, Houston, TX (US)

(73) Assignee: Exxon Mobil Chemical Patents, Inc., Houston, TX (US)

(*) Notice: Subject to any disclaimer, the term of this patent is extended or adjusted under 35 U.S.C. 154(b) by 26 days.

(21) Appl. No.: 10/870,512

(22) Filed: Jun. 17, 2004

(65) Prior Publication Data

US 2004/0236166 A1 Nov. 25, 2004

Related U.S. Application Data

(62) Division of application No. 10/138,223, filed on May 2, 2002, now Pat. No. 6,770,792.
(60) Provisional application No. 60/288,101, filed on May 2, 2001.

(51) Int. Cl.[7] .................................................. C07C 5/27
(52) U.S. Cl. ........................ 585/319; 585/477; 585/481
(58) Field of Search ................................ 585/319, 477, 585/481

(56) References Cited

U.S. PATENT DOCUMENTS

| | | |
|---|---|---|
| 4,269,813 A | 5/1981 | Klotz |
| 4,899,011 A | 2/1990 | Chu et al. |
| 4,954,325 A | 9/1990 | Rubin et al. |
| 5,015,794 A | 5/1991 | Reichmann |
| 5,227,552 A | 7/1993 | Chang et al. |
| 5,689,027 A | 11/1997 | Abichandani et al. |
| 5,705,726 A | 1/1998 | Abichandani et al. |

FOREIGN PATENT DOCUMENTS

| | | |
|---|---|---|
| WO | WO 99/38936 A1 | 8/1999 |
| WO | WO 01/30942 A1 | 5/2001 |

*Primary Examiner*—Thuan Dinh Dang

(57) ABSTRACT

A xylene isomerization process is disclosed in which any ethylbenzene in the feed is removed, either by dealkylation or isomerization, in a separate reactor upstream of the xylene isomerization reactor and the xylene isomerization catalyst is contained in the same reactor, typically a clay treater, as that used to accommodate the olefin removal catalyst. In certain cases, a single catalyst may be used to effect both xylene isomerization and olefin removal.

10 Claims, No Drawings

XYLENE ISOMERIZATION

CROSS REFERENCE TO RELATED APPLICATIONS

This application is a divisional of U.S. application Ser. No. 10/138,223 filed May 2, 2002, now U.S. Pat. No. 6,770,792; which claims priority to U.S. Provisional No. 60/288,101, filed May 2, 2001, which is fully incorporated herein by reference.

FIELD OF THE INVENTION

This invention is directed to a xylene isomerization process.

BACKGROUND

Para-xylene is a valuable chemical feedstock which may be derived from mixtures of $C_8$ aromatics separated from such raw materials as petroleum naphthas, particularly reformates, usually by selective solvent extraction. The $C_8$ aromatic fractions from these sources vary quite widely in composition but will usually contain 10 to 32 wt. % ethylbenzene (EB) with the balance, xylenes, being divided between approximately 50 wt. % meta and 25 wt. % each of para and ortho.

Individual isomer products may be separated from the naturally occurring mixtures by appropriate physical methods. Ethylbenzene may be separated by fractional distillation although this is a costly operation. Ortho-xylene may be separated by fractional distillation, and is so produced commercially. Para-xylene may be separated from the mixed isomers by fractional crystallization or selective adsorption (e.g., the Parex process).

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence an important feature of any commercial xylene isomerization process is the ability to convert ethylbenzene in the feed to useful products while simultaneously minimizing any conversion of xylenes to other compounds.

One known method for removing ethylbenzene from a $C_8$ aromatic stream is by dealkylation in which the ethylbenzene is converted to benzene and ethylene, with the latter normally being hydrogenated to produce ethane. Another known method for removing ethylbenzene is by isomerization to produce additional xylenes, normally through the intermediate step of saturating the ethylbenzene to produce naphthenes. In the past, a single catalyst was used to effect both xylene isomerization and ethylbenzene conversion, but this necessarily involved compromising between the different catalytic requirements of the two reactions. More recently, processes have been developed which employ separate catalysts tailored specifically for the different catalytic functions.

For example, U.S. Pat. No. 4,899,011 describes a xylene isomerization process employing ethylbenzene dealkylation, in which a $C_8$ aromatic feed, which has been depleted in its para-xylene content, is contacted with a two component catalyst system. The first catalyst component selectively converts the ethylbenzene by deethylation, while the second component selectively isomerizes the xylenes to increase the para-xylene content to a value at or approaching the thermal equilibrium value. The first catalyst component comprises a Constraint index 1–12 molecular sieve, such as ZSM-5, which has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury, whereas the second component comprises a Constraint Index 1–12 molecular sieve which has an ortho-xylene sorption time of less than 10 minutes under the same conditions. In one preferred embodiment, the first catalyst component is ZSM-5 having a crystal size of at least 1 micron and the second catalyst component is ZSM-5 having a crystal size of 0.02–0.05 micron. Each catalyst component also contains a hydrogenation component, preferably a platinum group metal.

An improvement over the process of U.S. Pat. No. 4,899,011 is described in U.S. Pat. No. 5,689,027 in which the first catalyst component in the two component system is preselectivated by coking, or more preferably by deposition of a, surface coating of silica, to increase its ortho-xylene sorption time to greater than 1200 minutes under the same conditions as cited in the '011 patent. Using such a system it is found that high ethylbenzene dealkylation rates can be achieved with significantly lower xylene losses than obtained with the process of the '011 patent.

Although the first and second catalyst components of the systems described in U.S. Pat. Nos. 4,899,011 and 5,689,027 can be housed in separate reactors, these processes are usually practiced in a single reactor in which the different components form separate beds in, for example, a fixed, stacked bed reactor. In contrast, U.S. Pat. No. 5,705,726 describes a similar process in which the ethylbenzene dealkylation step is performed in a separate reactor from that used for the subsequent xylene isomerization step. In theory, such a two reactor system offers significant advantages over a stacked bed system in that it allows the operating conditions as well as the catalyst properties to be tailored for the different reactions involved. In this way, it should be possible to operate at high ethylbenzene conversion while the xylene isomerization step is conducted at the milder conditions necessary to minimize reduce xylene losses. In practice, however, two reactor systems have generally not been adopted at least in part because of the increased capital cost of installing a second reactor and associated equipment.

The present invention seeks to provide a process which allows xylene isomerization and ethylbenzene conversion to be conducted in separate reactors without significant increase in capital cost by utilizing space within an existing reactor to accommodate the xylene isomerization catalyst. In particular, the invention is based on the realization that the product from the xylene isomerization step is normally fed to a clay treater to effect removal of any trace olefins in the product and that recent advances in olefin removal catalysts have significantly reduced the amount of catalyst required in the clay treater. As a result the clay treater provides reactor space which is already available in a conventional aromatics plant and which is suitable for accommodating a xylene isomerization catalyst. In addition, since the clay treater is operated at mild conditions compared with those employed in conventional xylene isomerization processes, the xylene losses can be reduced to very low levels.

SUMMARY OF THE INVENTION

Accordingly, the invention resides in one aspect in a process for isomerizing xylenes in a feed containing xylenes, which process comprises the step of contacting the feed with an isomerization catalyst under conditions effective to isomerize xylenes in the feed, wherein said isomerization catalyst is contained in a reactor which contains a further catalyst effective under said conditions to remove olefins in said feed.

Preferably, said conditions are such as to maintain said feed at least partially in the liquid phase.

Preferably, said conditions include a temperature of about 250° F. to about 500° F. (about 120° C. to about 260° C.), a pressure of about 50 to about 1000 psig (445 to 7000 kPa) and WHSV of about 0.1 to about 100.

More preferably, said conditions include a temperature of about 320° F. to about 450° F. (about 160° C. to about 232° C.), a pressure of about 100 to about 500 psig (790 to 3550 kPa) and WHSV of about 1 to about 30.

Preferably, said isomerization catalyst comprises a porous crystalline material selected from ZSM-5, MCM-22, MCM-36, MCM-49 and MCM-56.

Preferably, said isomerization catalyst has an alpha value greater than 300.

Preferably, said further catalyst comprises a porous crystalline material having pores and/or surface pockets defined by a ring of ten or more tetrahedrally coordinated atoms.

Preferably, said further catalyst comprises MCM-22.

Alternatively, said further catalyst comprises clay.

In another aspect, the invention resides in a process for isomerizing a feed which contains ethylbenzene and xylene, which process comprises the steps of:

(a) contacting the feed with a first catalyst in a first reactor under ethylbenzene conversion conditions, wherein the first catalyst is effective under said ethylbenzene conversion conditions to convert ethylbenzene in said feed and produce an ethylbenzene-depleted product; and then (b) contacting the ethylbenzene-depleted product with a second catalyst in a second reactor separate from the first reactor under conditions effective to isomerize xylenes in the feed, wherein said second reactor also contains a third catalyst effective under the conditions in said second reactor to remove olefins in said feed.

In yet another aspect, the invention resides in a process for isomerizing a feed which contains ethylbenzene and xylene, which process comprises the steps of:

(a) contacting the feed with a first catalyst in a first reactor under ethylbenzene conversion conditions, wherein the first catalyst is effective under said ethylbenzene conversion conditions to convert ethylbenzene in said feed and produce an ethylbenzene-depleted product; and then (b) contacting the ethylbenzene-depleted product with a second catalyst in a second reactor separate from the first reactor under conditions effective to isomerize xylenes in the feed and also remove olefins in said feed, wherein the conditions in said second reactor include a temperature of about 250° F. to about 500° F. (about 120° C. to about 260° C.), a pressure of about 50 to about 1000 psig (445 to 7000 kPa) and WHSV of about 0.1 to about 100.

In one embodiment of the invention, said first catalyst converts ethylbenzene by dealkylation. In such a case, the first catalyst preferably comprises an intermediate pore molecular sieve, such as ZSM-5, and has an ortho-xylene sorption time of greater than 50 minutes, and more preferably greater than 1200 minutes, based on its capacity to sorb 30% of the equilibrium capacity of ortho-xylene at 120° C. and an ortho-xylene partial pressure of 4.5±0.8 mm of mercury. The first catalyst would normally also contain a hydrogenation component, such as platinum, palladium and/or rhenium.

In an alternative embodiment of the invention, the first catalyst converts ethylbenzene by isomerization to xylenes. In such a case, the first catalyst is preferably selected from the group consisting of platinum on alumina, platinum-containing, potassium-exchanged zeolite L, platinum-containing mordenite, platinum-containing SAPO-11 and platinum-containing ETS-10.

DETAILED DESCRIPTION OF THE INVENTION

The present invention provides process for isomerizing xylenes in a $C_8$ aromatics feedstock in which the xylene isomerization step is conducted in the same reactor as that used to remove olefins from the feedstock. In an existing isomerization plant, this reactor would be the clay treater conventionally used for olefin removal from the isomerized product, either by replacement of the clay with a molecular sieve catalyst requiring significantly less catalyst volume or by filling available space in the clay treater. In a grass roots plant, the reactor could be designed to accommodate the xylene isomerization catalyst together with a clay and/or a molecular sieve olefin removal catalyst. It is also possible that a single catalyst could be used that would effectively remove olefins as well as effect xylene isomerization.

Normally the $C_8$ aromatics feedstock will also contain ethylbenzene and hence must be subjected to an ethylbenzene conversion step prior to xylene isomerization/olefin removal. In this case, the ethylbenzene conversion step is conducted in a separate reactor from the reactor used to effect the xylene isomerization and olefin removal.

Feedstock

In general, any aromatic $C_8$ mixture containing xylene may be used as the feed to the process of this invention. Generally, such a mixture will typically have an ortho-xylene content in the approximate range of 0 to 35 weight percent, a meta-xylene content in the approximate range of 20 to 95 weight percent and a para-xylene range of 0 to 15 weight percent. In addition, the feed will also normally contain ethylbenzene, typically in an amount between about 5 to about 60 weight percent. The feed in addition to the above aromatic $C_8$ mixture may contain non-aromatic hydrocarbons, i.e., naphthenes and paraffins in an amount up to 30 weight percent. In a preferred embodiment, the invention provides means to process a mixture of $C_8$ aromatics such as that derived from catalytic reforming of a petroleum naphtha to a mixture of reduced ethylbenzene content and increased content of para-xylene. The invention is particularly effective in treating a para-xylene lean mixture of $C_8$ aromatics to increase the para-xylene concentration up to approximately the thermal equilibrium level.

Ethylbenzene Conversion

If the $C_8$ aromatics feedstock contains a significant quantity of ethylbenzene, the feedstock is subjected to an ethylbenzene conversion step prior to xylene isomerization and olefin removal. The ethylbenzene conversion step is conducted in a first reactor separate from and upstream of the reactor used to effect xylene isomerization and olefin removal.

In a first and preferred embodiment of the invention, the ethylbenzene conversion step is effected by deethylation to produce benzene and light gas (normally ethane). Suitable catalysts for converting ethylbenzene by deethylation include intermediate pore size molecular sieves, which typically have a pore size of about 5 to less than about 7 Angstroms and are generally characterized by having a Constraint Index within the approximate range of 1 to 12. The method by which Constraint Index is determined is described fully in U.S. Pat. No. 4,016,218, incorporated herein by reference for details of the method. Examples of intermediate pore size molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein.

The molecular sieve employed in the dealkylation catalyst preferably has a relatively high acid activity, as measured by having an alpha value of at least 50, more typically of about 100 to about 500 and preferably of about 100 to about 300. The alpha test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

The molecular sieve used in the ethylbenzene dealkylation catalyst is preferably associated with a hydrogenation-dehydrogenation component. Examples of such components include the oxide, hydroxide, sulfide, or free metal (i.e., zerovalent) forms of Group 8 metals (i.e., Pt, Pd, Ir, Rh, Os, Ru, Ni, Co and Fe), Group 6 metals (i.e, Cr, Mo, W), Group 14 metals (i.e., Sn and Pb), Group 15 metals (i.e., Sb and Bi), and Group 7 metals (i.e., Mn, Tc and Re). Combinations of catalytic forms of such noble or non-noble metals, such as combinations of Pt with Sn, may be used. The metal is preferably in a reduced valence state. The reduced valence state of the metal may be attained, in situ, during the course of the reaction, when a reducing agent, such as hydrogen, is included in the feed to the reaction.

In one preferred embodiment of the invention, the hydrogenation-dehydrogenation component is a noble metal (i.e., Pt, Pd, Ir, Rh, Os and Ru) and most preferably is platinum. In a further preferred embodiment of the invention, the hydrogenation-dehydrogenation component is an early transition metal, such as molybdenum, tungsten, rhenium and/or manganese, most preferably rhenium.

The hydrogenation/dehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetraamine platinum complexes, platinum chloride, tin sulfate and tin chloride. The metal may be incorporated in the form of a cationic, anionic or neutral complex such as $Pt(NH_3)_4^{2+}$ and cationic complexes of this type will be found convenient for exchanging metals onto the molecular sieve. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. Anionic complexes such as the metatungstate, permanganate or perrhenate ions are also useful for impregnating metals onto the molecular sieves. After incorporation of the metal, the catalyst can then be filtered, washed with water and calcined at temperatures of from about 250 to about 500° C.

The amount of the hydrogenation-dehydrogenation component is suitably from about 0.001 to about 10 percent by weight, e.g., from about 0.1 to about 5 percent by weight, e.g, from about 0.1 to about 2 percent by weight, although this will, of course, vary with the nature of the component, with less of the highly active noble metals, particularly platinum, being required than of the less active base metals.

In addition, it may be desirable to combine the molecular sieve dealkylation catalyst with another material resistant to the temperature and other conditions of the process. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

Improved results and, in particular reduced xylene losses, are obtained when the ethylbenzene dealkylation catalyst is arranged to have carefully controlled xylene diffusional properties. These properties can be identified by noting the time (in minutes) required for the catalyst to sorb 30% of its equilibrium capacity for ortho-xylene at 120° C. and at an ortho-xylene partial pressure of 4.5±0.8 mm of mercury, such a test being described in U.S. Pat. Nos. 4,117,026; 4,159,282; and Re. 31,782; each of which is incorporated by reference herein. In particular, the ethylbenzene dealkylation catalyst is preferably selected so as to have an ortho-xylene sorption time (in minutes) in excess of about 50 and preferably greater than about 1200, but less than 10,000.

The desired xylene diffusion properties of the ethylbenzene dealkylation catalyst component can be achieved in a number of ways. For ortho-xylene diffusion times at or near the minimum value of 50 minutes, the selection of a large crystal form of the molecular sieve used in the catalyst, that is, having an average crystal size in excess of 1 micron, may be sufficient. However, to achieve higher diffusivity values, it may be desirable to selectivated the first catalyst component by deposition on the surface of the catalyst particles of a layer of coke and/or an oxide, such as silica, which is inert under the process conditions experienced in use. Where the catalyst particles are selectivated both large crystal size and medium crystal size (having a crystal size of 0.2–0.5 micron) molecular sieves can be used.

Where the ethylbenzene dealkylation catalyst component is to be selectivated with silica, this is conveniently achieved by subjecting the catalyst to one or more treatments with an organosilicon compound in a liquid carrier, each treatment being followed by calcination of the treated material in an oxygen-containing atmosphere, e.g., air. Such a multiple selectivation procedure is described in U.S. Pat. No. 5,476,823, the entire contents of which are incorporated herein by reference.

The organosilicon compound which is used to selectivate the first catalyst component may be, for example, a silicone, a siloxane, a silane or mixtures thereof. These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferably, the kinetic diameter of the organosilicon compound, which is used to preselectivate the molecular sieve, is larger than the molecular sieve pore diameter, in order to avoid entry of the organosilicon compound into the molecular sieve pores and any concomitant reduction in the internal activity of the molecular sieve.

Preferred organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

Preferably, the liquid carrier for the organosilicon compound is an organic compound, such as a linear, branched or cyclic hydrocarbon having five or more, especially 7 or more, carbon atoms per molecule, e.g., an alkane, such as heptane, octane, nonane or undecane. The boiling point of the organic compound, e.g., alkane, may be greater than about 70° C. Mixtures of low volatility organic compounds, such as hydrocracker recycle oil, may be employed as carriers. Particularly preferred organic carriers are decane and dodecane.

Following each impregnation with the organosilicon compound, the catalyst is calcined at a rate of from about 0.2° C./minute to about 5° C./minute to a temperature greater than 200° C., but below the temperature at which the crystallinity of the molecular sieve is adversely affected. This calcination temperature will generally be below 600° C. and preferably is within the approximate range of 350 to 550° C. The duration of calcination at the calcination temperature may be from 1 to 24 hours, e.g., from 2 to 6 hours.

In addition to, or in place of, silica selectivation, the first catalyst component may be subjected to coke selectivation. This optional coke selectivation typically involves contacting the catalyst with a thermally decomposable organic compound at an elevated temperature in excess of the decomposition temperature of said compound, but below the temperature at which the crystallinity of the molecular sieve is adversely affected. This contact temperature may be, for example, less than about 650° C. Organic materials, which may be used for this coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the U.S. Pat. No. 4,117,026, incorporated by reference herein. By using a combination of silica selectivation followed by coke selectivation, the number of organosilicon impregnation treatments required to achieve a particular xylene diffusivity can be reduced.

Where the ethylbenzene conversion is effected by dealkylation, suitable conditions for the ethylbenzene conversion step include a temperature of about 350° C. to about 600° C., a pressure of about 10 kPa to about 30 kPa, a WHSV of about 3 to about 20, and a hydrogen to hydrocarbon mole ratio of about 0.5:1 to about 5.0:1.

In a second embodiment of the invention, the ethylbenzene conversion step is effected by isomerization so as to increase the overall xylene concentration in the feedstock. Ethylbenzene isomerization is a known process and can be conducted over a number of non-acidic or low acidity catalysts. Examples of suitable ethylbenzene isomerization catalysts include platinum on alumina, platinum-containing, potassium-exchanged zeolite L (including the zeolite-bound zeolite L disclosed in, for example, U.S. Pat. No. 6,040,259), platinum-containing mordenite, platinum-containing SAPO-11 (see, for example, U.S. Pat. No. 4,740,650) and platinum-containing titanosilicate ETS-10 (see, for example, U.S. Pat. No. 4,853,202). Other suitable catalysts include the MgAPSO materials, such as MgAPSO-31, as disclosed in U.S. Pat. Nos. 5,478,787 and 5,516,957 and platinum-exchanged, gallium-substituted ZSM-12 disclosed in U.S. Pat. Nos. 4,962,259 and 5,081,084. All the above patents are incorporated herein by reference.

Where the ethylbenzene conversion is effected by isomerization, suitable conditions for the ethylbenzene conversion step include a temperature of about 320° C. to about 440° C., a pressure of about 10 kPa to about 40 kPa, a WHSV of about 0.5 to about 15, and a hydrogen to hydrocarbon mole ratio of about 1.0:1 to about 6:1.

Xylene Isomerization/Olefin Removal

After the $C_8$ aromatics feedstock has been subjected to ethylbenzene conversion, the ethylbenzene-depleted product is fed to a separation system to remove $C_8$— by-products and then passed to a second reactor containing either (a) a xylene isomerization catalyst and a separate olefin removal catalyst, either as a mixture or more preferably, as separate beds in the same reactor, or (b) a single catalyst capable of both isomerizing the xylenes in the feedstock and removing olefins from the feedstock. In a preferred embodiment, the second reactor is a fixed bed reactor in which the xylene isomerization catalyst and olefin removal catalyst are in sequential beds, with the feedstock being cascaded between the beds without interstage separation. In a revamp of an existing xylene isomerization unit, the second reactor is preferably an existing clay treater.

Where the second reactor contains separate isomerization and olefin removal catalysts, the xylene isomerization component is preferably a molecular sieve selected from MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697), with MCM-49 being particularly preferred. The entire contents of the above references are incorporated by reference herein.

Alternatively, the xylene isomerization component can be one of the Constraint Index 1–12 molecular sieves described above as being suitable for use as the ethylbenzene dealkylation catalyst, in which case the molecular sieve is preferably ZSM-5.

In any event, the molecular sieve used as the xylene isomerization component should have a relatively high acid activity, since the conditions used the second reactor will generally be less severe than those conventionally employed in a xylene isomerization reactor. In particular, the xylene isomerization catalyst preferably has an alpha value greater than 300 and more preferably greater than 600.

The xylene isomerization catalyst preferably has an ortho-xylene sorption time of less than about 50 minutes and preferably less than about 10 minutes. This is typically achieved by using a small crystal size molecular sieve, having an average crystal size of 0.02–0.05 micron, as the active material of the catalyst.

Where separate isomerization and olefin removal catalysts are employed in the second reactor, the olefin removal catalyst can be a conventional clay catalyst or more preferably comprises a porous crystalline material having pores and/or surface pockets defined by a ring of ten or more tetrahedrally coordinated atoms. Examples of suitable porous crystalline materials for use as the olefin removal catalyst include ZSM-4 (U.S. Pat. No. 3,923,639), mordenite, ZSM-18 (U.S. Pat. No. 3,950,496), ZSM-20 (U.S. Pat. No. 3,972,983), zeolite beta (U.S. Pat. No. 3,308,069 and Re 28,341), faujasite, USY (U.S. Pat. No. 3,449,070), REY (U.S. Pat. No. 4,415,438), MCM-22, PSH-3, SSZ-25, MCM-36, MCM-49 and, MCM-56. Other suitable olefin removal catalysts include the mesoporous crystalline materials M41S (U.S. Pat. No. 5,102,643). Preferably, said olefin removal catalyst comprises MCM-22. The entire contents of the above references are incorporated by reference herein.

Preferably, the olefin removal catalyst has an alpha value less than 100.

Alternatively, a single catalyst may be used to effect both xylene isomerization and olefin removal. A suitable single catalyst would be MCM-22, PSH-3, SSZ-25, MCM-36, MCM-49 or MCM-56, with MCM-22 being particularly preferred.

The conditions in the second reactor are selected so as to be effective to isomerize the xylenes in the feedstock as well as to remove olefins without excessive undesirable side reactions. In general, therefore the conditions will be less severe than those employed in conventional xylene isomerization processes and in particular will be such as to maintain the feedstock at least partially in the liquid phase. Suitable conditions include conditions include a temperature of about 250° F. to about 500° F. (about 120° C. to about 260° C.), a pressure of about 50 to about 1000 psig (445 to 7000 kPa) and WHSV of about 0.1 to about 100. More preferably, said conditions include a temperature of about 320° F. to about 450° F. (about 160° C. to about 232° C.), a pressure of about 100 to about 500 psig (790 to 3550 kPa) and WHSV of about 1 to about 30. In general, the processes in the second reactor are conducted in the absence of added hydrogen.

In the second reactor, the xylenes in the feedstock are isomerized so that the concentrations of the para-, ortho- and meta-isomers are moved towards their thermodynamic equilibrium values, while trace olefins are alkylated with aromatic components in the feedstock to produce a heavy ($C_9$+) alkylaromatic component. The effluent from the second reactor is then treated to isolate para-xylene and/or other desirable xylene(s) and remove the heavy alkylaromatic component. Thus, for example, the effluent can be fed to a para-xylene recovery unit, such as a crystallizer, a membrane separation unit, or a selective adsorption unit, so that the para-xylene may be isolated and recovered. Subsequently, after removal of the heavy alkylaromatic fraction, the para-xylene depleted effluent can be recycled to the second reactor.

The invention will now be more particularly described with reference to the following Examples.

EXAMPLE 1

A two-bed catalyst system in a single reactor was used to isomerize a stream of para-depleted mixed xylenes and ethylbenzene, as well as to remove olefins from the stream. The feed was a sample from the raffinate of a commercial para-xylene separation unit, to which 0.25 wt % 1-octene had been added.

The catalyst system included a top bed comprising a ZSM-5 catalyst and a bottom bed comprising a self-bound MCM-22 catalyst. The ZSM-5 used in the top bed catalyst had a $SiO_2$:$Al_2O_3$ molar ratio of approximately 16:1 and average crystal size of about 0.01 to 0.02 micron, and was synthesized in an autoclave. The as-synthesized crystals were heated under nitrogen to 482° C. and held at this temperature for 3 hours, then exchanged with 1.0 N $NH_4NO_3$ solution for one hour at room temperature. The crystals were then filtered, rinsed thoroughly with deionized water, and then dried in air at 120° C. The dried material was heated to 482° C. in a mixture of 5% $N_2$ and 95% air, held for 2 hours at 482° C., then heated to 538° C. in 100% air and held at 538° C. for six hours. The resulting material contained less than 500 ppm Na and had an alpha value of 880. The self-bound MCM-22 catalyst was manufactured by first crystallizing the MCM-22 zeolite, forming the MCM-22 zeolite into an extrudate, in the absence of a binder, and then calcining the extrudate. The calcined extrudate was next contacted with an aqueous solution of ammonium ions to exchange alkali metal ions with ammonium ions. The exchanged catalyst was then calcined to provide the acidic hydrogen form. Self-bound MCM-22 has been measured to have an alpha value of 390.

Four grams of the powdered ZSM-5 catalyst were loaded into a ¾" outer diameter reactor on top of one gram of the MCM-22 catalyst, with a layer of quartz wool separating the two catalyst beds. The liquid feed was used to fill the reactor and the reactor pressure raised to 200 psig (4240 kPa), before the temperature of the reactor was increased to 210° C. Flow of the feed was set to 20 g/hr corresponding to a WHSV for the ZSM-5 bed of 5 $hr^{-1}$ and for the MCM-22 bed of 20 $hr^{-1}$. Four hours after the reactor had reached temperature, a product sample was taken and the results are summarized in Table 1.

TABLE 1

| Component | Feed | Product |
|---|---|---|
| $C_5-$ | 0.0 | <0.1 |
| Benzene | <0.1 | 0.9 |
| Toluene | 1.7 | 2.4 |
| Ethylbenzene | 15.9 | 14.5 |
| Para-Xylene | 0.6 | 11.6 |
| Meta-Xylene | 62.7 | 50.1 |
| Ortho-Xylene | 18.1 | 17.8 |
| $C_9$ Aromatics | 0.2 | 0.6 |
| $C_6$–$C_9$ Non-Aromatics | 0.8 | 0.5 |
| $C_{10}+$ | <0.1 | 1.5 |
| Bromine Index | 83 | 8 |

The results in Table 1 example clearly show that both isomerization and olefin reduction occurred using the two-bed catalyst system described above. Para-xylene increased substantially by isomerization of mostly meta-xylene, whereas the bromine index dropped by over 90% and no 1-octene was detected in the product.

EXAMPLE 2

In order to achieve both isomerization and olefin reduction for an ethylbenzene-depleted feed at liquid-phase conditions, the same catalyst system and feed described in Example 1 were used at 450° F. (230° C.) and 200 psig (4240 kPa). Four grams of ZSM-5 catalyst were loaded on top of one gram of MCM-22 catalyst, separated by quartz wool, inside a 0.75 inch (1.9 cm) outer diameter reactor tube. The reactor was liquid-filled and brought to temperature as described in Example 1. The ethylbenzene-depleted feed was blended so as to represent a para-xylene-depleted feed where ethylbenzene conversion had been performed catalytically (U.S. Pat. No. 5,998,688). Approximately 0.25 wt % 1-octene was added to the feed. The feed flow rate was 8 g/hr so that the WHSV across the ZSM-5 bed was 2 $hr^{-1}$ and the WHSV across the MCM-22 bed was 8 $hr^{-1}$. After approximately 90 hours of operation, the product was analyzed and the results are summarized in Table 2.

TABLE 2

| Component | Feed | Product |
|---|---|---|
| $C_5-$ | 0.0 | 0.1 |
| Benzene | 6.4 | 6.5 |
| Toluene | 3.3 | 4.5 |
| Ethylbenzene | 1.5 | 1.6 |
| Para-Xylene | 11.3 | 20.1 |
| Meta-Xylene | 50.0 | 46.1 |
| Ortho-Xylene | 27.3 | 19.5 |
| $C_9$ Aromatics | 0.1 | 0.6 |
| $C_6$–$C_9$ Non-Aromatics | 0.3 | 0.1 |
| $C_{10}+$ | <0.1 | 1.0 |
| Bromine Index | 256 | 3 |

The data shown above demonstrate clearly that both isomerization and olefin removal occur within the reactor for an ethylbenzene-depleted feed. In fact, the para-xylene yield indicates over a 90% approach towards equilibrium.

EXAMPLE 3

Combined isomerization and olefin reduction were studied using a para-xylene-depleted aromatic hydrocarbon feed at vapor-phase conditions. The catalyst system used was the same as in Examples 1 and 2, comprising a ZSM-5 bed on top and an MCM-22 bed on the bottom. Both catalysts have been described in prior examples. Two grams of powder ZSM-5 were loaded into a ½ inch (1.3 cm) outer diameter reactor tube on top of 0.5 grams of MCM-22 catalyst immersed in sand, with a wire mesh separating the two catalysts. The reactor was pressured to 14.3 psig, followed by introduction of the para-xylene-depleted hydrocarbon feed. In order to demonstrate olefin reduction, the hydrocarbon feed had been spiked with 0.25% 1-octene. Hydrogen was also fed in a 1:1 molar ratio with the hydrocarbon. The flow rate of hydrocarbon was 4 g/hr, which corresponded to a WHSV of 2 $hr^{-1}$ across the ZSM-5 bed and 8 $hr^{-1}$ across the MCM-22 bed. The test was conducted at 230° C. (450° F.) and the results are summarized in Table 3.

TABLE 3

| Component | Feed | Product |
|---|---|---|
| $C_5-$ | 0.0 | 0.1 |
| Benzene | <0.1 | 0.1 |
| Toluene | 1.6 | 1.7 |
| Ethylbenzene | 15.7 | 15.4 |
| Para-Xylene | 0.6 | 10.4 |
| Meta-Xylene | 62.8 | 53.1 |
| Ortho-Xylene | 18.1 | 18.0 |
| $C_9$ Aromatics | 0.2 | 0.3 |
| $C_6$–$C_9$ Non-Aromatics | 0.8 | 0.4 |
| $C_{10}+$ | 0.1 | 0.5 |
| Bromine Index | 83 | 22 |

The results in Table 3 demonstrate that both isomerization and olefin removal occurred over this catalyst system at vapor-phase conditions. The isomerization was on the order of the liquid-phase examples. Remaining olefins in the product are generally attributed to C2–C4 light gas olefins shown by gas chromatography.

What is claimed is:

1. A process for isomerizing a feed which contains ethylbenzene and xylene, which process comprises the steps of:
    (a) contacting the feed with a first catalyst in a first reactor under ethylbenzene conversion conditions, wherein the first catalyst is effective under said ethylbenzene conversion conditions to convert ethylbenzene in said feed and produce an ethylbenzene-depleted product; and then
    (b) contacting the ethylbenzene-depleted product with a second catalyst in a second reactor separate from the first reactor under conditions effective to isomerize xylenes in the feed, wherein said second reactor also contains a third catalyst effective under the conditions in said second reactor to remove olefins in said feed by alkylation of the olefins with aromatic compounds to produce a $C_{9+}$ alkylaromatic component.

2. The process of claim 1, wherein said first catalyst converts ethylbeuzene primarily by dealkylation.

3. The process of claim 2, wherein said first catalyst comprises an intermediate pore molecular sieve having a Constraint Index of about 1 to about 12.

4. The process of claim 3, wherein said molecular sieve is selected from the group consisting of ZSM-5; ZSM-11; ZSM-12; ZSM-22; ZSM-23; ZSM-35; ZSM-48, ZSM-57; and ZSM-58.

5. The process of claim 3, wherein said first catalyst has an ortho-xylene sorption time of greater than 50 minutes, based on its capacity to sorb 30% of the equilibrium capacity of ortho-xylene at 120° C. and an ortho-xylene partial pressure of 4.5±0.8 mm of mercury.

6. The process of claim 3, wherein said first catalyst has an ortho-xylene sorption time of greater than 1200 minutes, based on its capacity to sorb 30% of the equilibrium capacity of ortho-xylene at 120° C. and an ortho-xylene partial pressure of 4.5±0.8 mm of mercury.

7. The process of claim 1, wherein the first catalyst converts ethylbenzene primarily by isomerization to xylenes.

8. The process of claim 7, wherein the first catalyst is selected from the group consisting of platinum on alumina, platinum-containing, potassium-exchanged zeolite L, platinum-containing mordenite, platinum-containing SAPO-11, platinum-containing ETS-10, MgAPSO-31 and platinum-exchanged, gallium-substituted ZSM-12.

9. A process for isomerizing a feed which contains ethylbenzene and xylene, which process comprises the steps of:

(a) contacting the feed with a first catalyst in a first reactor under ethylbenzene conversion conditions, wherein the first catalyst is effective under said ethylbenzene conversion conditions to convert ethylbenzene in said feed and produce an ethylbeuzene-depleted product; and then (b) contacting the ethylbenzene-depleted product with a second catalyst in a second reactor separate from the first reactor under conditions effective to isomerize xylenes in the feed and also remove olefins in said feed by alkylation of the olefins with aromatic compounds to produce a $C_{9+}$ alkylaromatic component, wherein the conditions in said second reactor include a temperature of about 250° F. to about 500° F. (about 120° C. to about 260°C.), a pressure of about 50 to about 1000 psig (about 445 to about 7000 kPa) and WHSV of about 0.1 to about 100.

10. The process of claim 9, wherein said second catalyst comprises MCM-22.

* * * * *